US008101410B2

(12) United States Patent
Saradhi

(10) Patent No.: US 8,101,410 B2
(45) Date of Patent: Jan. 24, 2012

(54) SELECTION MARKER SYSTEM AND METHOD FOR SCREENING A CHOLINE TOLERANT PLANT CELL

(75) Inventor: Peddisetty Pardha Saradhi, Noida (IN)

(73) Assignee: Entelechon GmbH, Bad Abbach (DE)

( * ) Notice: Subject to any disclaimer, the term of this patent is extended or adjusted under 35 U.S.C. 154(b) by 543 days.

(21) Appl. No.: 12/096,451

(22) PCT Filed: Dec. 4, 2006

(86) PCT No.: PCT/EP2006/011801
§ 371 (c)(1),
(2), (4) Date: Dec. 19, 2008

(87) PCT Pub. No.: WO2007/065697
PCT Pub. Date: Jun. 14, 2007

(65) Prior Publication Data
US 2009/0170093 A1 Jul. 2, 2009

(30) Foreign Application Priority Data

Dec. 8, 2005 (EP) .................................... 05090335

(51) Int. Cl.
*C12N 5/04* (2006.01)
*C12N 15/82* (2006.01)
*A01H 1/04* (2006.01)
(52) U.S. Cl. ........................................ 435/419; 435/468
(58) Field of Classification Search .......................... None
See application file for complete search history.

(56) References Cited

U.S. PATENT DOCUMENTS

| 6,756,525 | B1 | 6/2004 | Murata | |
|---|---|---|---|---|
| 7,026,528 | B2 * | 4/2006 | Cheng et al. | ................. 800/294 |

FOREIGN PATENT DOCUMENTS

| WO | WO 98/26081 | 6/1998 |
|---|---|---|
| WO | WO 98/30702 | 7/1998 |

OTHER PUBLICATIONS

Prasad et al, Plant Science, vol. 159, pp. 233-242, 2000.*
Prasad et al., Plant Science, (2000), vol. 159, pp. 233-242, cited in the IDS filed Oct. 30, 2009.*
Geneback Accession No. AY589052, Apr. 28, 2004.*
Patent Cooperation Treaty, "International Search Report", PCT/EP2006/011801, May 7, 2007, 4 pages.
Patent Cooperation Treaty, "Written Opinion of the International Searching Authority", PCT/EP2006/011801, 7 pages.
Assad F et al., "Cauliflower mosaic virus P35S promoter activity in *Escherichia coli*", *Molecular General Genetics*, vol. 223, 517-520. (1990).
Auer CA, "Tracking genes from seed to supermarket: techniques and trends", *Trends in Plant Science*, vol. 8, 591-597. (2003).
Barcelo P et al., "Transgenic cereal (tritordeum) plants obtained at high efficiency by microprojectile bombardment of inflorescence tissue", *The Plant Journal*, vol. 5, 583-592.(1994).
Bartsch D et al., "Genetic evidence for the origin of Californian wild beets (genus Beta)", *Theoretical and Applied Genetics*, vol. 99, 1120-1130. (1999).
Bartsch D et al., "Ecological aspects of transgenic sugar beet: transfer and expression of herbicide resistance in hybrids with wild beets", *Euphytica*, vol. 91 , 55-58. (1996).
Bertolla F et al., "Horizontal gene transfers in the environment: natural transformation as a putative process for gene transfers between transgenic plants and microorganisms", *Research in Microbiology*, vol. 150, 375-384. (1999).
Bevan MW et al., "A chimaeric antibiotic resistance gene as a selectable marker for plant cell transformation", *Nature*, vol. 304, 184-187. (1983).
Brasilerio Acm et al., "Marker genes for in vitro selection of transgenic plants", *Journal of Plant Biotechnology*, vol. 3, 113-121. (2001).
Che FS et al., "Stimulation of photosynthesis and growth of photoautotrophically cultured plant cells by choline and its analogs", *Plant Cell Reports*, vol. 12, 691-697. (1993).
Clemente TE et al., "Progeny analysis of glyphosate selected transgenic soybeans derived from Arobacterium-mediated transformation", *Crop Science*, vol. 40, 797-803. (2000).
Coghlan A., "Weeds do well out of modified crops", *New Scientist* Aug. 17, 2011. (2002).
Comai L et al., "Expression in plants of aroA gene from *Salmonella typhimurium* confers tolerance to glyphosate", *Nature*, vol. 317, 741-744. (1985).
Comai L et al., "An altered aroA gene product confers resistance to the herbicide glyphosate", *Science*, vol. 221, 370-371. (1983).
Dale PJ et al., "Potential for the environmental impact of transgenic crops", *Nature Biotechnology*, vol. 20, 567-574. (2002).

(Continued)

*Primary Examiner* — Eileen B O Hara
(74) *Attorney, Agent, or Firm* — Viksnins Harris& Padys PLLP

(57) ABSTRACT

The present invention relates to a selection marker system for distinguishing genetically modified plant cells from wild-type plant cells comprising (a) a nucleic acid sequence coding for choline oxidase, choline monooxygenase and/or choline dehydrogenase for genetically modifying at least a part of a plant and; (b) at least a part of a wild-type plant of the same plant species, wherein the part of the plant which is genetically modified by the nucleic acid sequence coding for choline oxidase, choline monooxygenase and/or choline dehydrogenase is capable of surviving in a medium containing choline at a concentration which is toxic to the wild-type plant. Furthermore, the invention relates to a method for screening and/or identifying a choline tolerant plant cell and the use of a nucleic sequence coding for a choline oxidase, choline monooxygenase and/or choline dehydrogenase as a selection marker for choline tolerance.

9 Claims, 3 Drawing Sheets

OTHER PUBLICATIONS

Daniell H, "The next generation of genetically engineered crops for herbicide and insect resistance: containment of gene pollution and resistant insects", *AgBiotechNet* 024, vol. 1, 1-7. (1999).

Daniell H et al., "Containment of herbicide resistance through genetic engineering of the chloroplast genome", *Nature Biotechnology*, vol. 16, 345-348. (1998).

Darmency M et al., "Spontaneous hybridizations between oilseed rape and wild radish", *Molecular Ecology*, vol. 7, 1467-1473. (1998).

Dawla B, "Gene revolution and genetic contamination", *The Daily Star*, 4(217), 3 pages. (2004).

Day A, "Antibiotic resistance genes in transgenic plants: their origins, undesirability and technologies for their elimination from genetically modified crops", *Transgenic plants: current innovations and future trends*, 111-156. (2003).

De Block M et al., "Engineering herbicide resistance in plants by expression of a detoxifying enzyme", *The EMBO Journal*, vol. 6, 2513-2518. (1987).

Eber F et al., "Spontaneous hybridization between a male-sterile oilseed rape and two weeds", *Theoretical and Applied Genetics*, vol. 88, 362-368. (1994).

Flavell RB et al., "Selectable marker genes: safe for plants?", *Bio/Technology*, vol. 10, 141-144. (1992).

Flothmann S et al., "Of maize and men", *EMBO Reports*, vol. 2, 644-647 (2001).

Frello S et al., "Inheritance of rapeseed (*Brassica napus*)—specific RAPD markers and a transgene in the cross *B. juncea* x (*B. juncea* x *B. napus*)", *Theoretical and Applied Genetics*, vol. 91, 236-241. (1995).

Fuchs RL et al., "Safety Assessment of the Neomycin Phosphotransferase-II (NPTII) protein", *Bio/Technology*, vol. 11, 1543-1547. (1993).

Gawer M et al., "Comparison between a choline-tolerant *Nicotiana tabacum* cell line and the corresponding wild type. I. Growth, thermosensitivity and lipid composition", *Plant Physiology and Biochemistry*, vol. 26, pp. 323-331 (1988).

Guadagnuolo R et al., "Gene flow from wheat (*Triticum aestivum* L.) to jointed goatgrass (*Aegilops cylindrica* Host.), as revealed by RAPD and microsatellite markers", *Theoretical and Applied Genetics*, vol. 103, 1-8. (2001).

Haldrup A, et al., "The xylose isomerase gene from *Thermoanaerobacterium thermosulfurogenes* allows effective selection of transgenic plant cells using D-xylose as the selection agent", *Plant Molecular Biology*, 37, 287-296. (1998).

He Z et al., "*Phosphomannose-isomerase* (pmi) gene as a selectable marker for rice transformation via Agrobacterium", *Plant Science*, vol. 166, 17-22. (2004).

Hendley JO., "Eradication of resident bacteria of normal human skin by antimicrobial ointment", *Antimicrobial Agents in Chemotherapy*, 47, 1988-1990. (2003).

Herrera-Estrella L et al., "Chimeric genes are dominant selectable markers in plant cells", *The EMBO Journal*, vol. 2, 987-995. (1983).

Jaiwal PK et al., "Strategies to deal with the concern about marker genes in transgenic plants: Some environment-friendly approaches", *Current Science*, vol. S3, 128-136. (2002).

Joersbo M, "Advances in the selection of transgenic plants using non-antibiotic marker genes", *Physiologia Plantarum*, vol. 111, 269-272. (2001).

Joersbo M et al., "Analysis of mannose selection used for transformation of sugar beet", *Molecular Breeding*, vol. 4, 111-117. (1998).

Joersbo M et al., "Parameters interacting with mannose selection employed for the production of transgenic sugar beet", *Physiologia Plantarum*, vol. 105, 109-115. (1999).

Kaeppler HF et al., "Transgenic oat plants via visual selection of cells expressing green fluorescent protein", *Plant Cell Reports*, vol. 19, 661-666. (2000).

Lefol E et al., "Gene dispersal from transgenic crops. II. Hybridization between oilseed rape and the wild hoary mustard", *Sexual Plant Reproduction*, vol. 9, 189-196. (1996).

Lilius G et al., "Enhanced NaCl stress tolerance in transgenic tobacco expressing bacterial choline dehydrogenase", *Nature Biotechnology*, vol. 14, No. 2, 177-180 (1996).

Lucca P et al., "Effective selection and regeneration of transgenic rice plants with mannose as selective agent", *Molecular Breeding*, vol. 7, 43-49. (2001).

Mikkelsen TR et al., "The risk of crop transgene spread", *Nature*, vol. 380, 31. (1996).

Mudd SH et al., "Synthesis of methylated ethanolamine moieties. Regulation by choline in Lemna", *Plant Physiology*, vol. 90, 296-305. (1989).

Mudd SH et al., "Synthesis of methylated ethanolamine moieties. Regulation by choline in soybean and carrot", *Plant Physiology*, vol. 90, 306-310. (1989).

Murashige T et al., "A revised medium for rapid growth and bioassay with tobacco tissue cultures", *Physiologia Plantarum*, vol. 15, 473-497. (1962).

Nap JP et al., "Biosafety of kanamycin-resistant transgenic plants", *Transgenic Research*, vol. 1, 239-249. (1992).

Nash D et al., "Effect of proline, betaine and some other solutes on the heat stability of mitochondrial enzymes", *Australian Journal of Plant Physiology*, vol. 9, 47-57. (1982).

Negrotto D et al., "The use of phosphomannose-isomerase as a selectable marker to recover transgenic maize plants (Zea mays L.) via Agrobacterium transformation", *Plant Cell Reports*, vol. 19, 798-803. (2000).

Nielsen KM et al., "Horizontal gene transfer from transgenic plants to terrestrial bacteria-arare event?", *FEMS Microbiology Reviews*, vol. 22, 79-103. (1998).

Prasad Kvsk et al., "Enhanced tolerance of transgenic Brassica Juncea to Choline confirms succeddful expression of the bacterial codA gene", *Plant Science*, vol. 159, 233-242. (2000).

Puchta H, "Marker-free transgenic plants", *Plant Cell, Tissue and Organ Culture*, vol. 74, 123-134. (2003).

Shah DM et al., "Engineering herbicide tolerance in transgenic plants", *Science*, vol. 233, 478-481. (1986).

Storey R et al., "Quaternary ammonium compounds in plants in relation to salt resistance", *Phytochemistry*, vol. 16, 447-453. (1977).

Summers PS et al., "Choline synthesis in spinach in relation to salt stress", *Plant Physiology*, vol. 103, 1269-1276. (1993).

Thimm T et al., "Contribution of the earthworm *Lumbricus rubellus* (Annelida, Oligochaeta) to the establishment of plasmids in soil bacterial communities", *Microb. Ecol.*, vol. 41, 341-351. (2001).

Wang AS et al., "A mannose selection system for production of fertile transgenic maize plants from protoplasts", *Plant Cell Reports*, vol. 19, 654-660. (2000).

Wang WC et al., "Development of a novel Agrobacterium—mediated transformation method to recover transgenic *Brassica napus* plants", *Plant Cell Resorts*, vol. 22, 274-281. (2003).

Weretilnyk EA et al., "Enzymes of choline synthesis in spinach. Response of phospho-Base N-methyltransferase activities to light and salinity", *Plant Physiology*, vol. 109, 1085-1091. (1995).

Wolfenbarger LL et al., "The ecological risks and benefits of genetically engineered plants", *Science*, vol. 290, 2088-2093. (2000).

Wright GD, "Bacterial resistance to antibiotics: Enzymatic degradation and modification", *Advanced Drug Delivery Reviews*, vol. 57, 1451-1470. (2005).

Yilmaz JL et al., "Enhanced stress tolerance in *Escherichia coli* and *Nicotiana tabacum* expressing a betaini aldehyde dehydrogenase/choline dehydrogenase fusion protien", *Biotechnology Progress*, vol. 18, pp. 1176-1182 (2002).

Zhang P et al., "PIG-mediated cassava transformation using positive and negative selection", *Plant Cell Reports*, vol. 19, 1041-1048. (2000).

Zhang P et al., "Efficient production of transgenic cassava using negative and positive selection", *Transgenic Research*, vol. 9, 405-415. (2000).

\* cited by examiner

SELECTION MARKER SYSTEM AND METHOD FOR SCREENING A CHOLINE TOLERANT PLANT CELL

RELATED APPLICATIONS

This application is a National Stage application under 35 U.S.C. §371 and claims the benefit of priority of International Application No. PCT/EP2006/011801 having an International Filing Date of Dec. 4, 2006 which claims the benefit of priority of European Patent Application Serial No. 05090335.0 filed on Dec. 8, 2005, which are hereby incorporated by reference herein in their entireties.

FIELD OF THE INVENTION

The present invention relates to the technical field of selection marker systems and screening methods.

BACKGROUND OF THE INVENTION

Use of markers to identify the transformed cells/morphogenic units is an essential component of transformation technology (Puchta 2003). Selection of transformed cells, which are generally few in number and are mingled with a large number of untransformed cells, is possible only through use of selective agents, which can rapidly inhibit growth and/or kill the non-transformed cells. This has been traditionally accomplished through the introduction of antibiotic or herbicide resistance genes, enabling the selection of transgenic cells on media supplemented with the corresponding antibiotic/herbicide (Brasileiro and Dusi 1999; Puchta 2003).

Antibiotics are well documented to severely curtail cellular metabolism in prokaryotes and also affect plant cells by interfering with essential metabolic events in mitochondria and plastids, in particular chloroplasts (Nap et al. 1992; Brasileiro and Aragao 2001; Day 2003). These double membrane organelles involved in energy transduction have been well documented to play a vital role in cellular metabolism and regulation of morphogenesis/developmental events in plant cells. Antibiotics like neomycin are used in medicine for killing pathogenic bacteria such as Staphylococci (Hendley and Ashe 2003). The antibiotic resistance marker genes have potency to make antibiotics ineffective, usually, by phosphorylation (Brasileiro and Aragão 2001; Wright 2005). Similarly, herbicide resistance marker genes such as aroAlepsps and bar genes, used as markers to select the trans-formed cells have the potential to detoxify herbicides such as glyphosate (Comai et al., 1983, 1985; Shah et al. 1986; Clemente et al. 2000) and phosphinothricin (De Block et al. 1987; Barcelo et al. 1994), respectively.

The antibiotic/herbicide resistance marker genes are widely classified in the category of negative selection markers (Day 2003; He et al. 2004). Earlier investigations involved raising choline oxidase transgenic genotypes of Brassica juncea cv. Varuna exploiting one such antibiotic resistance marker, neomycin phosphotransferase II (npt II). Presence of npt II in transformed cells/morphogenic units enables them to resist exogenous kanamycin as product of this gene, neomycin phosphotransferase phosphorylates active kanamycin to an inactive/ineffective form (Bevan et al. 1983; Herrera-Estrella et al. 1983; Brasileiro and Aragão 2001).

However, escape of antibiotic resistance markers like npt II into pathogenic bacteria can make them resistant to the antibiotic, rendering the use of the antibiotics ineffective in medicine (Assad and Signer 1990; Flavell et al., 1992; Nap et al. 1992; Fuchs et al., 1993; Daniell et al. 1998; Haldrup et al. 1998; Nielsen et al. 1998, Bertolla and Simonet 1999; Thimm et al. 2001; Dawla 2004). Flow of herbicide resistance marker genes into weeds can lead to emergence of 'Superweeds' (Eber et al. 1994; Frello et al. 1995; Bartsch and Pohl-Orf 1996; Lefol et al. 1996; Mikkelsen et al. 1996; Darmency et al. 1998; Bartsch and Ellstrand 1999; Daniell 1999; Wolfenbarger and Phifer 2000; Flothmann and van Aken 2001; Guadagnuolo et al. 2001; Coghlan, 2002; Dale et al. 2002; Auer 2003). In a nutshell, it can be presumed that the escape of antibiotic/herbicide marker genes from transgenics can lead to an ecological disturbance.

Growing concern about the use of marker genes that are ecologically unfit has forced researchers to look for alternate eco-friendly markers that can be safely used (Haldrup et al. 1998; Joersbo et al. 1998; Wang et al. 2000; Zhang et al. 2000; Zhang and Puonti-Kaerlas 2000; Lucca et al. 2001; Jaiwal et al. 2002; Puchta 2003; He et al. 2004). One of the approaches to identify eco-friendly markers focused attention on exploitation of certain essential biomolecules that can have a drastic negative effect on cellular metabolism and various developmental events, if present at levels above the threshold limit. Such biomolecules have been placed in the category of positive selection markers (Joersbo and Okkels 1996; Haldrup et al. 1998; Joersbo et al. 1999; Kaeppler et al. 2000; Negrotto et al. 2000; Wang et al. 2000, 2003; Joersbo 2001; Lucca et al. 2001; Wright et al. 2001; He et al. 2004).

Choline plays a vital role in several important cellular events such as (i) maintenance of structural and functional integrity of the membranes by regulating the levels of PtdCho, often referred to as lecithin, and (ii) synthesis of an important compatible solute, glycinebetaine (GB) in plants (e.g. sugarbeet, spinach and barley), animals (e.g. rats) and microorganisms (e.g. E. coli). In general, choline has been demonstrated to play an important role in promoting plant growth, especially in the induction and growth of roots (Che et al. 1993). By regulating the production of glycinebetaine, choline even plays an important role in protecting cells against abiotic stresses such as salinity and drought (Summers and Weretilnyk 1993).

The perfect tuning in the levels of choline could be due to its toxicity to certain metabolic events whenever it is present in excess. Higher concentrations of choline have been shown to inhibit plant growth. For instance, high levels of choline inhibit activities of some enzymes such as Rubisco, glyceraldehyde-3-phosphate dehydrogenase, isocitrate dehydrogenase and malate dehydrogenase associated with some important metabolic events (Nash et al. 1982).

Choline is universally present in higher organisms (Prasad et al. 2000) and is primarily involved in maintaining structural and functional integrity of the membranes (Storey and Wyn Jones 1977). Living systems possess perfect mechanisms to regulate the level of free choline in their cells (Weretilnyk et al. 1995). In the presence of exogenous choline at levels as low as 50 µM, a marked decline in the specific activities of the enzymes involved in choline biosynthesis was reported by Mudd and Datko (1989a).

Based on the above-cited prior art there still remains a need for economically friendly selection markers which can be used in field surroundings and environments. Such selection markers must not bear the risk of escape from the plant, since unregulated and uncontrolled spread of markers in the environment is undesired.

SUMMARY OF THE INVENTION

The present invention is directed to a selection marker system for distinguishing genetically modified plant cells from wild-type plant cells comprising (a) a nucleic acid sequence coding for choline oxidase, choline monooxygenase and/or choline dehydrogenase for genetically modifying at least a part of a plant and;
(b) at least a part of a wild-type plant of the same plant species,
  wherein the part of the plant which is genetically modified by the nucleic acid sequence coding for choline oxidase, choline monooxygenase and/or choline dehydrogenase is capable of surviving in a medium containing choline at a concentration which is toxic to the wild-type plant.

During the present investigation efforts were made to compare the ability of wild type, non glycinebetaine synthesizers (i.e. plant species lacking glycinebetaine pathway) and choline oxidase (codA$_{ps}$) transgenic genotypes of *Brassica* (harboring codA gene isolated earlier, GenBank accession number AY589052 and exhibiting glycinebetaine synthesis) to withstand high levels of choline.

The inventors clearly prove that the cells of plant species lacking glycinebetaine pathway are extremely sensitive to choline while the cells of transgenic lines of these plant species expressing choline oxidase, choline monooxygenase and/or choline dehydrogenase attained tolerance towards choline at levels that are lethal to wild type cells.

The inventors have demonstrated for the first time that choline oxidase, choline monooxygenase and choline dehydrogenase can be used as a marker gene for plant transformation.

These results were completely unexpected, since it was shown in the prior art that exogenous choline concentrations of about 50 µM inhibit specific activities of enzymes and thereby influence the normal growth of plants. The inventors were able to demonstrate that concentrations of exogenous choline which are increased more than 1,000 fold in comparison to the prior art levels can be successfully tolerated by plants harbouring choline oxidase, choline monooxygenase and/or choline dehydrogenase.

Additionally, it has been surprisingly found that a combination of choline oxidase, choline monooxygenase and choline dehydrogenase is particularly suitable to render the genetically modified plant cell choline tolerable, even in concentrations which are high above the threshold at which choline is toxic to the wild type plant.

The present invention further concerns a method for screening and/or identifying a choline tolerant plant cell, comprising the steps of
(a) genetically modifying a plant cell of interest with a nucleic acid coding for choline oxidase, choline monooxygenase and/or choline dehydrogenase;
(b) culturing the genetically modified plant cell in a medium containing choline at a concentration which is toxic to a wild-type of a plant cell of interest; wherein survival of the genetically modified plant cell is indicative of a choline tolerant plant cell.

DETAILED DESCRIPTION OF THE INVENTION

Figure 1:
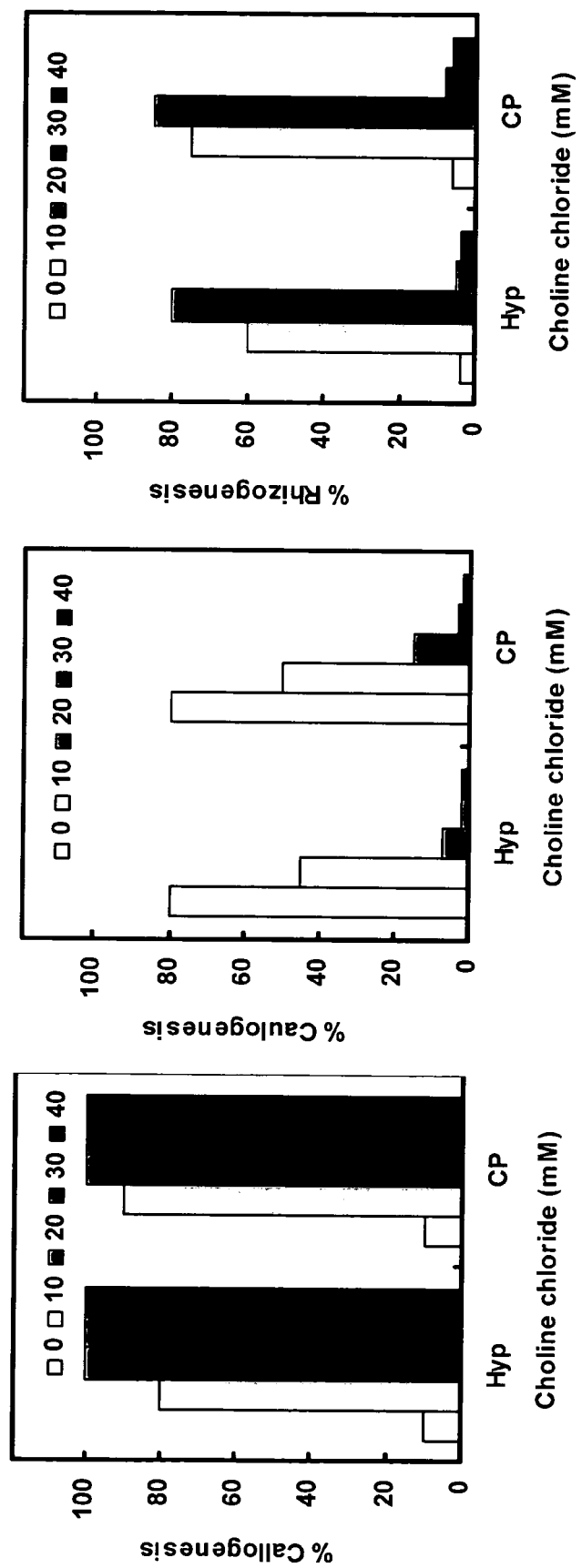
FIG. 1 shows the effect of choline chloride on callogenesis, caulogenesis and rhizogenesis of hypocotyl (Hyp) and cotyledonary petiolar (CP) explants of *Brassica juncea* cv. Varuna. Observations recorded 20 d after inoculating on MS medium supplemented with BAP (1 mg/l), NAA (1 mg/l) and AgNO$_3$ (3.4 mg/l) in presence of various concentrations of choline chloride (0, 10, 20, 30 and 40 represent concentration of choline chloride in mM).

Preferred embodiments of the present invention will be described in further detail below.

In a preferred embodiment of the present invention the choline concentration in the medium is up to approx. 60 mM, preferably 5 to 60 mM, more preferably approx. 10 to 40 mM, even more preferred approximately 20 to 40 mM, even more preferred approx. 30 to 40 mM, most preferred approx. 40 mM. It has been shown that plants comprising an exogenously derived nucleic acid sequence coding for choline oxidase, choline monooxygenase and/or choline dehydrogenase can survive in a medium containing choline concentrations which are lethal to the wild type of plant.

Therefore, the selection marker system is a positive selection marker system, which is ecologically friendly and can be used in the environment without the disadvantages of environmental systems of the prior art.

The nucleic acid sequence coding for choline oxidase is preferably isolated from *Arthrobacter* sp. Choline monooxygenase is preferably isolated from a plant and choline dehydrogenase is derived from an animal or bacteria in particular *E. coli*.

The inventors have demonstrated that the present invention is particularly applicable to plants from the species *Brassica, Nicotiana, Cicer* and *Arabidopsis*.

In another preferred embodiment the genetic modification is done by a method selected from the group consisting of plant cell transformation, transfection, electroporation, DNA injection and/or cell fusion.

Choline is provided in the form of a suitable salt, in particular choline chloride, choline acetate, choline sulphate and/or choline nitrate.

It is particularly preferred if the part of the plant is selected from the group consisting of a single cell, seedling, root, seed, shoot, leaf, hypocotyl, cotyledon, petiole, cotyledonary leaf and callus.

Furthermore, the invention is directed to a method for screening and/or identifying a choline tolerant plant cell, comprising the steps of
(a) genetically modifying a plant cell of interest with a nucleic acid coding for choline oxidase, choline monooxygenase and/or choline dehydrogenase;
(b) culturing the genetically modified plant cell in a medium containing choline at a concentration which is toxic to a wild-type of a plant cell of interest;
wherein survival of the genetically modified plant cell is indicative of a choline tolerant plant cell.

Additionally, the invention is directed to the use of a nucleic acid sequence coding for a choline oxidase, choline monooxygenase and/or choline dehydrogenase as a selection marker for choline tolerance.

The present invention uses choline as a selective agent in a positive selection system. Table 1 shows effective concentrations of various selective agents in positive selection systems.

TABLE 1

Effective concentrations of various selective agents in positive selection systems

| Selective agent | Selection concentration (mg/l) | Plant Species | Reference |
|---|---|---|---|
| Mannose | 360 | *Arabidopsis thaliana* | Todd and Tague (2001) |
| | 5000 | *Oryza sativa* L. | Lucca et al. (2001) |
| | 9900 | *Beta vulgaris* L. | Joersbo et al. (1999) |
| | 10000 | *Beta vulgaris* L. | Joersbo et al. (1998) |
| | 10000 | *Manihot esculenta* Crantz | Zhang and Pounti-Kaerlas (2000) |
| | 10000 | *Zea mays* L. | Negrotto et al. (2000) |
| | 10000 | *Zea mays* L. | Wright et al. (2001) |
| | 15000 | *Triticum aestivum* L. | Wright et al. (2001) |
| | 20000 | *Zea mays* L. | Wang et al. (2000) |
| | 25000 | *Oryza sativa* L. | He et al. (2004) |
| | 40000 | *Manihot esculenta* Crantz | Zhang et al. (2000) |
| Xylose | 3750 | *Solanum tuberosum* L. | Haldrup et al. (1998) |
| | 15000 | *Lycopersicon esculentum* L. | Haldrup et al. (1998) |
| | 20000 | *Nicotiana tabacum* L. | Haldrup et al. (1998) |
| Choline | 5584 | *Brassica juncea* L. | Present Investigations |
| | 5584 | *Nicotiana tabacum* L. | Present Investigations |

Choline has been shown to be a particularly useful selective agent, since it is much cheaper in comparison to other selective agents, like kanamycin or hygromycin. Table 2 shows a comparison of the relative costs of various selective agents.

TABLE 2

Relative costs of various selective agents

| Selective agent | Selection concentration (mg/l) | [A]Cost/g | | Selection cost/l | |
|---|---|---|---|---|---|
| | | US$ | Rs. | US$ | Rs. |
| Kanamycin | 20-150 | 24.6 | 1070.1 | 0.49-3.69 | 21.40-160.51 |
| Hygromycin | 5-50 | 370.6 | 16121.1 | 1.85-18.53 | 80.60-806.05 |
| Phosphinothricin | 5-10 | 262.53 | 11420 | 1.31-2.62 | 57.10-114.20 |
| Mannose | 10000-40000 | 1.324 | 57.59 | 13.24-52.96 | 575.94-2303.76 |
| Xylose | 3750-20000 | 1.24 | 53.94 | 4.65-24.80 | 202.27-1078.80 |
| Choline | 5584 | 0.21 | 9.135 | 1.17 | 51.01 |

[A]As per the price list of Sigma-Aldrich Fine Chemicals (USA), 2004-05. (1 US$ = Rs. 43.50)

Materials and Methods Employed
Plant Material

Seeds of *Brassica juncea* cv. Varuna were obtained from Dr. Rajani Raman, Department of Genetics, Indian Agricultural Research Institute (IARI), Pusa, New Delhi, India. *Brassica juncea* L. Czern & Coss (brown mustard) (*Brassicaceae*, AABB), an amphidiploid (2n=36) is one of the major oil crops grown in India and is widely referred to as Indian mustard. Cultures of *Nicotiana tabacum* cv. Petit Havana SR1 were obtained from Dr. P. Ananda Kumar, Department of Biotechnology, Indian Agricultural Research Institute (IARI), Pusa, New Delhi, India.

Agrobacterium Mediated Transformation of *Brassica* Explants with Choline Oxidase (codA) Gene The codA gene was isolated in the inventors' laboratory from local strain of *Arthrobacter globiformis* (GenBank accession number AY589052, hereafter referred as $codA_{ps}$ gene) and cloned into pPZP200lox(npt 11) vector (obtained from Dr. Deepak Pental, Department of Genetics, South Campus, University of Delhi, New Delhi, India). The resultant vector named as pSG was electroporated into *Agrobacterium tumefaciens* strain GV3101. Hypocotyl and cotyledonary petiolar explants were excised from 6 d old sterile seedlings were transformed using *Agrobacterium tumefaciens* strain GV3101/pSG/$codA_{ps}$.

For caulogenesis hypocotyl and cotyledonary petiolar explants from 6 d old seedlings of *Brassica juncea* cv. Varuna were inoculated on MS medium (Murashige and Skoog 1962) supplemented with BAP (6-Benzylaminopurine) (1.0 mg/l), NAA (α-Naphthaleneacetic acid) (1.0 mg/l), $AgNO_3$ (Silver nitrate) (3.4 mg/l) (hereafter referred as Shoot Induction Medium). Selection Medium comprised of kanamycin (20 mg/l) and cefotaxime (250 mg/l) in addition to BAP (1.0 mg/l), NAA (1.0 mg/l), $AgNO_3$ (3.4 mg/l). For shoot multiplication (through axillary bud sprouting) and elongation the shoots were first transferred to MS basal medium for 15 days and then transferred to MS medium supplemented with BAP (2.5 mg/l).

Effect of Choline
Effect of Choline Chloride on Caulogenesis in *Brassica juncea* cv. Varuna Efforts were made during present investigations to investigate the effect of choline chloride/potassium chloride on the regeneration potential of *Brassica juncea* cv. Varuna. Hypocotyl and cotyledonary petiolar explants from 6 d old seedlings of *Brassica juncea* cv. Varuna were inoculated on Shoot Induction Medium with varying concentrations of choline chloride/potassium chloride (0, 10, 20, 30 and 40 mM).

Effect of Choline on Shoots
*Brassica juncea*

To test the effect of choline, ~2 cm long shoots of wild type and independent $codA_{ps}$ transgenic lines with 4-5 leaves derived through multiple shooting (axillary bud sprouting) were placed on MS medium supplemented with varying concentrations of choline chloride (0, 5, 10, 20, 40 and 60 mM).

*Nicotiana tabacum* cv. Petit Havana SR1

The shoots of *Nicotiana tabacum* obtained by multiplying the shoots regenerated from the leaf segments on MS medium supplemented with BAP (2 mg/l) were used to evaluate the effect of various concentrations of choline (0, 20 and 40 mM). In one set of experiments uniformly looking ~1 cm long shoots were taken while in a second set of experiments a bunch of 6-8 shoots were used.

Effect of Choline on Seed Germination and Seedling Growth

As the shoots of codA$_{ps}$ transgenic lines grew happily in the presence of choline at concentrations that were lethal to wild type shoots, seed germination and seedling growth (that are otherwise well known to be sensitive to abiotic stresses/toxic levels of organic compounds) of the independent transgenic lines and wild type were compared. T$_2$ seeds of various independent homozygous transgenic lines of *Brassica juncea* cv. Varuna and wild type were inoculated on MS medium supplemented with various concentrations of filter sterilized choline chloride (0, 20 and 40 mM). Homozygous transgenic genotypes were identified based on 100 percent germination of T$_2$ seed of various independent transformed lines in the presence of 50 mg/l kanamycin.

In order to evaluate the effect of choline on seed germination and early seedling growth under the conditions that provide little/no osmotic shock the seeds were also inoculated on half strength MS medium devoid of sucrose and all other organics (MGM) supplemented with various concentrations of filter sterilized choline chloride (0, 20 and 40 mM).

Results

Effect of Choline Chloride on Caulogenesis in *Brassica juncea* cv. Varuna

80% of both hypocotyl and cotyledonary petiolar explants exhibited optimal caulogenesis (in terms of 100 percent cultures showing shoot induction and number of shoots per culture as well as the good quality of shoots) on MS medium supplemented with BAP (1.0 mg/l), NAA (1.0 mg/l) and AgNO$_3$ (3.4 mg/l). Effect of varying concentrations of choline chloride (0, 10, 20, 30 and 40 mM) on caulogenesis from hypocotyl and cotyledonary petiolar explants on MS medium supplemented with BAP (1.0 mg/l), NAA (1.0 mg/l) and AgNO$_3$ (3.4 mg/i) was tested. The results obtained are summarized in FIG. 1. The presence of choline suppressed shoot induction from both hypocotyl and cotyledonary petiolar explants on the shoot induction medium. However, choline did not cause any significant alteration in callogenesis i.e. callus induction at lower concentrations but in general lower concentrations of choline promoted rhizogenesis. 100% of cultures exhibited callogenesis in the presence of 40 mM choline.

In general, cotyledonary petiolar explants possessing part of cotyledonary leaf lamina expanded over 6-fold and simultaneously exhibited shoot induction from the petiolar cut end on MS medium supplemented with BAP (1.0 mg/l), NAA (1.0 mg/l) and AgNO$_3$ (3.4 mg/l). Interestingly, besides suppressing caulogenesis from the cotyledonary petiolar explants choline also significantly curtailed the expansion of the cotyledonary leaves. In addition, the presence of choline in the medium also caused significant reduction in the green pigmentation of the cotyledonary petiolar explants. The degree of reduction in caulogenesis, reduction in expansion of cotyledonary leaf explants and the extent of decline in green pigmentation increased distinctly with increase in the concentration of choline in the medium. Almost 100 percent of cotyledonary explants lost green pigmentation completely on medium with 40 mM choline.

Figure 2:
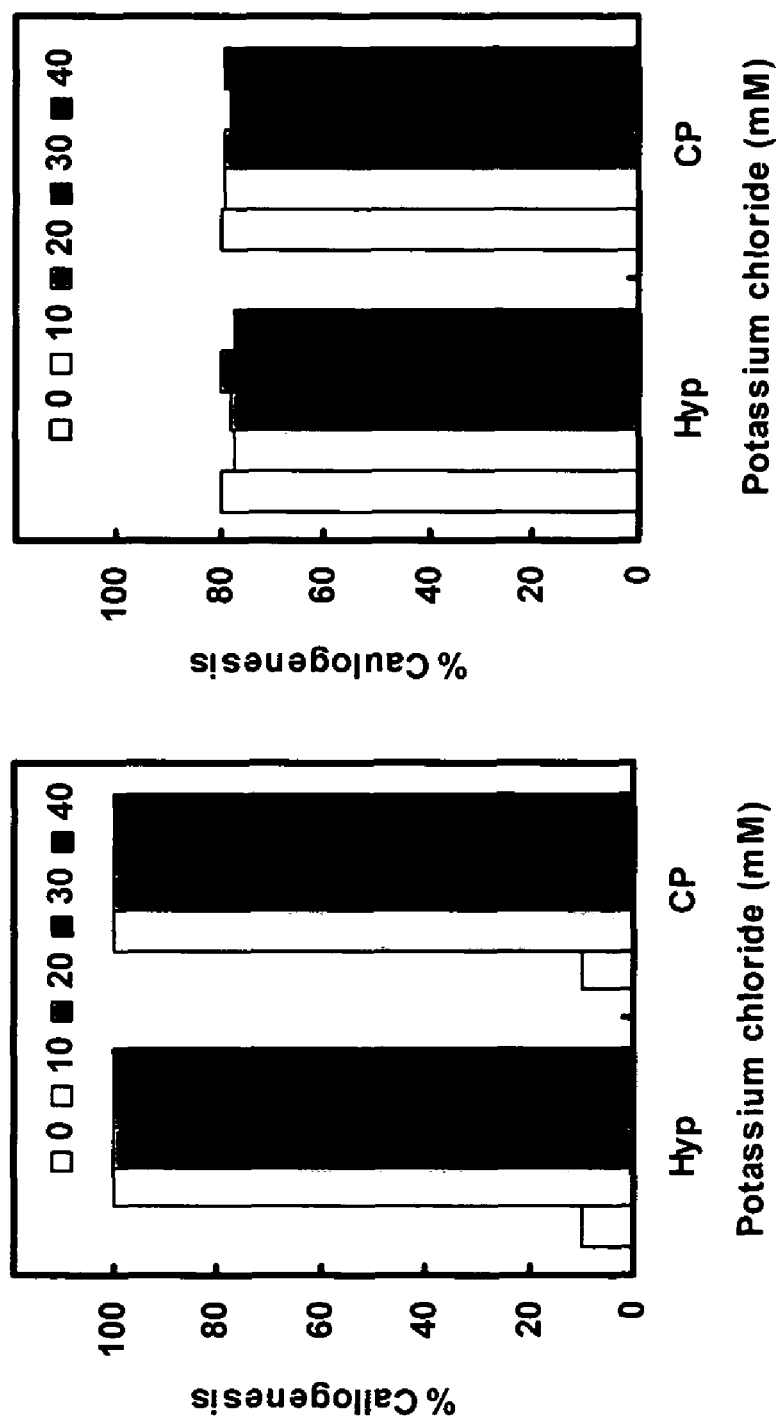
FIG. 2 shows the effect of potassium chloride on callogenesis, caulogenesis of hypocotyls (Hyp) and cotyledonary petiolar (CP) explants of *Brassica juncea* cv. Varuna. Observations recorded 20 d after inoculating on MS medium supplemented with BAP (1 mg/l), NAA (1 mg/l) and AgNO$_3$ (3.4 mg/l) in presence of various concentration of potassium chloride (0, 10, 20, 30 and 40 mM).

In order to evaluate if the effect observed above was due to choline or chloride, varying concentrations of potassium chloride (0, 10, 20, 30 and 40 mM) were used in place of choline chloride. As is clear from FIG. 2, no significant alteration was noted in shoot induction due to the presence of potassium chloride at any of the concentration tested. Further, presence of potassium chloride even at highest concentration did not cause any suppression in the expansion of cotyledons and/or alteration in green pigmentation. These results clearly demonstrated that the effect seen above were solely due to choline and not due to chloride.

Effect of Choline on Shoots

*Brassica juncea*

In order to test the effect of choline on shoots ~2 cm long with 4-5 leaves derived through multiple shooting (axillary bud sprouting) were used. For evaluating the potential of these shoots to withstand choline, the shoots were transferred to MS medium supplemented with varying concentrations of choline chloride (0, 5, 10, 20, 40 and 60 mM).

Interestingly, choline significantly curtailed the growth of shoots and the degree of suppression in growth increased with increase in the concentration of choline. The shoots grown in the presence of choline at a concentration of 20 mM and above exhibited loss in green pigmentation followed by browning/senescence leading to death within 15 d of their inoculation. The extent of senescence increased with time of exposure.

*Nicotiana tabacum*

In order to confirm if the choline toxicity is common to other plant systems, *Nicotiana tabacum*, one of the most popularly used plant system for transformation/testing the expression of transgenes was used. For this purpose, shoots of *Nicotiana tabacum* cv. Petit Havana SR1 were obtained by multiplying the shoots regenerated from the leaf segments on MS medium supplemented with 2 mg/l BAP. Two types of shoot explants were used for the present investigations to evaluate the effect of choline. In one set of experiments uniformly looking ~1 cm long shoots were used while in a second set of experiments a bunch of 6-8 shoots were inoculated on MS medium supplemented with varying concentrations of choline chloride (0, 20 and 40 mM).

It was clearly demonstrated that choline is equally toxic for the growth of shoots of *Nicotiana*, as seen in case of *Brassica*. Choline significantly curtailed shoot growth and the degree of damage was prominent with increase in its concentration. For instance, within 7 d of inoculation loss of green pigmentation followed by senescence/death was recorded in the shoots of *Nicotiana* in the presence of 40 mM choline. In the second type of shoots used for testing choline effect, one of the cultures exposed to 20 mM choline showed relatively good growth. This could be attributed to the reduced uptake of choline by one of the shoots from the bunch of shoots inoculated in the presence of choline.

Effect of Choline on Transgenic Shoots of *Brassica juncea*

In order to test whether introduction of the gene for choline oxidase into *Brassica juncea* cv. Varuna, enhanced its potential to withstand toxic levels of exogenously applied choline, shoots of four independent transformed lines (lines A, B, D and E) (~2 cm long with 4-5 leaves) were inoculated on MS medium supplemented with varying concentrations of choline chloride (0, 5, 10, 20, 40 and 60 mM). In contrast to wild type, the shoots of the independent transgenic lines were able to withstand choline even up to concentrations as high as 60 mM. The presence of choline at a level of 40 mM brought no significant alteration in the growth of the shoots of transgenic lines. Moreover, the growth of shoots of the transgenic lines (in terms of height and number of leaves borne) in presence of 20 and 40 mM choline was found to be similar to the shoots inoculated in the medium devoid of choline. However, at 60 mM choline, suppression in the growth of shoots of the transformed lines was observed but no loss in green pigmentation was evident.

The above observations demonstrated that the transformed lines of *Brassica juncea* cv. Varuna have enhanced potential to withstand toxic levels of choline as compared to wild type. Effect of Choline on Seed Germination and Seedling Growth As the shoots of codA transgenic lines attained inbuilt potential to grow happily in the presence of choline at concentrations that were found to be lethal to wild type shoots, it was felt wise to compare seed germination and seedling growth (that are otherwise well known to be sensitive to abiotic stresses/toxic levels of organic compounds) of the independent transgenic lines with that of wild type.

For these studies seeds from four homozygous transgenic lines (lines A, B, D and E) of $T_2$ generation were used. The homozygous genotypes were identified based on 100 percent germination of seed in the presence of 50 mg/l kanamycin (i.e. otherwise lethal to wild type/non-transgenic lines). In general, wild type genotype showed significant delay in seed germination on MS medium. The percent seed germination as well as seedling growth was suppressed significantly on MS medium supplemented with choline. The degree of decline in percent seed germination and reduction in seedling growth intensified with increase in concentration of choline in MS medium.

Four of the independent transgenic lines viz. A, B, D and E, showed significantly faster and 100 percent seed germination and seedling growth on MS medium supplemented with choline in comparison to wild type. Interestingly, 100 percent of the seed of all these four transgenic lines germinated at all the concentrations of choline tested. Further, seedling growth in the presence of 20 mM choline and below was comparable to those grown in the absence of choline. Although, there was slight reduction in the internodal length, a significant reduction in seedling growth was recorded on MS medium supplemented with 40 mM choline. However, in contrast to almost no/little seed germination and quick senescence of seedling of wild type in the presence of 40 mM choline, transgenic lines A, B, D and E showed 100 percent seed germination with significantly higher degree of early seedling growth.

A significant delay in seed germination and comparatively lesser seedling growth of wild type seed on full strength MS medium, led us to believe that the delay in seed germination and lower seedling growth in case of wild type could be due to high osmotic strength prevalent in full MS medium. In order to have a better comparison it was felt wise to evaluate the effect of choline on seed germination and early seedling growth under the conditions that provide little/no osmotic shock. For this purpose half strength MS medium devoid of sucrose and all other organics (hereafter referred to as MGM) supplemented with choline was used.

Seeds of wild type and all the transgenic lines germinated faster on MGM, the early seedling growth was hastened significantly on this medium in comparison to that recorded on full MS medium. However, the seed germination of four of the five transgenic lines tested was noted to be faster than that of wild type. Seeds of wild type germinated after 24 h but that of the transgenic lines germinated within 18 h of inoculation. The growth of the seedlings of the transgenic lines was faster than that of wild type. Moreover, growth of wild type seedlings on MGM was significantly superior to those grown on full strength MS medium.

Figure 3:
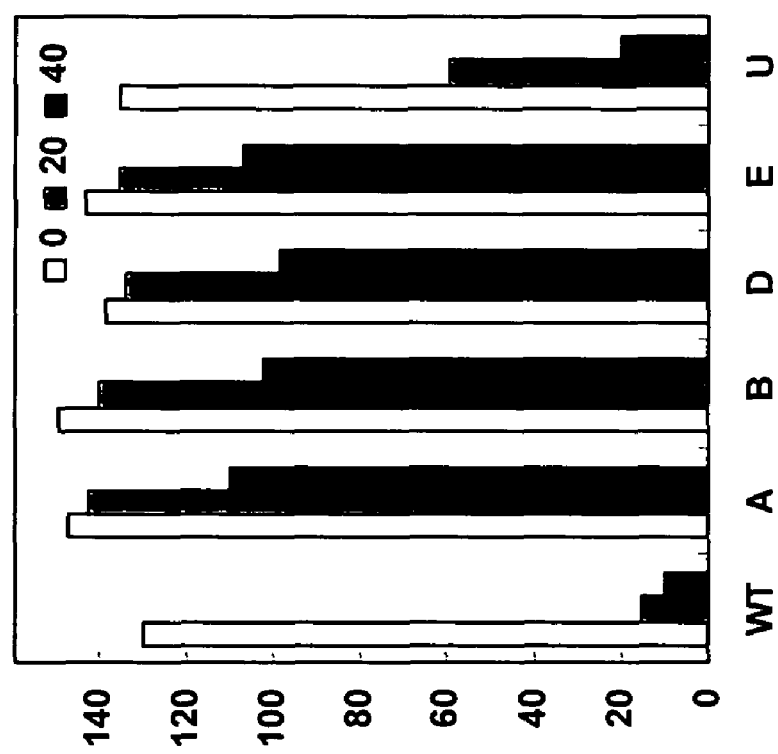
FIG. 3 shows the fresh weight of seedlings of various independent codA$_{ps}$ trans-genic lines (A, B, D, E and U) and wild type (WT) of *Brassica juncea* cv. Varuna, 30 d after inoculation of seeds on MGM supplemented with varying concentration of choline chloride (0, 20 and 40 mM).

The seed germination and early seedling growth of wild type was noted to be significantly curtailed in the presence of choline. The effect of choline toxicity was more pronounced with increase in concentration of choline in MGM. Four of the five transgenic lines tested proved to be superior to wild type at all the concentrations of choline tested (FIG. 3). Seed germination and early seedling growth of these four lines viz. A, B, D and E in the presence of $\leq 20$ mM choline was similar to that noted in absence of choline. However, in presence of 40 mM choline there was delay in seed germination as well as reduction in seedling growth in all these four transgenic lines in comparison to those grown in presence of 20 mM choline. Pigmentation of the seedlings grown in the presence of choline was similar to those raised in absence of choline.

Fresh weight of the wild type seedlings raised in the presence of 40 mM choline was 90% lower than those raised in absence of choline. On the contrary, fresh weight of four of the independent transgenic lines raised in the presence of 40 mM choline was only 25-30% lower than their respective controls.

REFERENCES

Assad F F and Signer E R (1990) Cauliflower mosaic virus P35S promoter activity in *Escherichia coli*. *Molecular General Genetics* 233, 517-520.

Auer C A (2003) Tracking genes from seed to supermarket: techniques and trends. *Trends in Plant Science* 8, 591-597.

Barcelo P, Hagel C, Becker D, Martin A and Lorz H (1994) Transgenic cereal (tritordeum) plants obtained at high efficiency by microprojectile bombardment of inflorescence tissue. *The Plant Journal* 5, 583-592.

Bartsch D and Ellstrand N C (1999) Genetic evidence for the origin of Californian wild beets (genus *Beta*). *Theoretical and Applied Genetics* 99, 1120-1130.

Bartsch D and Pohl-Orf M (1996) Ecological aspects of transgenic sugar beet: transfer and expression of herbicide resistance in hybrids with wild beets. *Euphytica* 91, 55-58.

Bertolla F and Simonet P (1999) Horizontal gene transfer in the environment: natural transformation as a putative process for gene transfer between transgenic plants and microorganisms. *Research in Microbiology* 150, 375-384.

Bevan M W, Flavell R B and Chilton M D (1983) A chimaeric antibiotic resistance gene as a selectable marker for plant cell transformation. *Nature* 304, 184-187.

Brasileiro A C M and Aragão F J L (2001) Marker genes for in vitro selection of transgenic plants. *Journal of Plant Biotechnology* 3, 113-121.

Brasileiro A C M and Dusi D M A (1999) Transformação genética de plantas. In 'Cultura de tecidos e transformação genética de plantas'. pp 679-735. (Brasilia, Embrapa-SPI/Embrapa-CNPH)

Che F S, Sato F, Hyeon S B, Isogai A, Yamada Y and Suzuki A (1993) Stimulation of photosynthesis and growth of photoautotrophically cultured plant cells by choline and its analogs. *Plant Cell Reports* 12, 691-697.

Clemente T E, LaVallee B J, Howe A R, Conner-Ward D, Rozman R J, Hunter P E, Broyles D L, Kasten D S and Hinchee M A (2000) Progeny analysis of glyphosate selected trans-genic soybeans derived from *Agrobacterium*-mediated transformation. *Crop Science* 40, 797-803.

Coghlan A (2002) Weeds do well out of modified crops. *New Scientist August* 17, 11.

Comai L, Facciotti D, Hiatt W R, Thompson G, Rose R E and Stalker D M (1985) Expression in plants of a mutant aroA gene from *Salmonella typhimurium* confers tolerance to glyphosate. *Nature* 317, 741-744.

Comai L, Sen L C and Stalker D M (1983) An altered aroA gene product confers resistance to the herbicide glyphosate. *Science* 221, 370-371.

Dale P J, Clarke B and Fontes E M G (2002) Potential for the environmental impact of transgenic crops. *Nature Biotechnology* 20, 567-574.

Daniell H (1999) The next generation of genetically engineered crops for herbicide and insect resistance: containment of gene pollution and resistant insects. *Ag Biotech Net* 024 1, 1-7.

Daniell H, Datta R, Varma S, Gray S and Lee S B (1998) Containment of herbicide resistance through genetic engineering of the chloroplast genome. *Nature Biotechnology* 16, 345-348.

Darmency H, Lefol E and Fleury A (1998) Spontaneous hybridizations between oilseed rapes and wild radish. *Molecular Ecology* 7, 1467-1473.

Dawla B (2004) Gene revolution and genetic contamination. *The Daily Star* 4 January 4, 217.

Day A (2003) Antibiotic resistance genes in transgenic plants: their origins, undesirability and technologies for their elimination from genetically modified crops. In 'Transgenic plants: current innovations and future trends'. pp 111-156. (Horizon Scientific Press: UK)

De Block M, Botterman J, Vandewiele M, Dockx J, Thoen C, Gossele V, Movva N R, Thompson C, Van Montagu M and Leemans J (1987) Engineering herbicide resistance in plants by expression of a detoxifying enzyme. *The EMBO Journal* 6, 2513-2518.

Eber F, Chèvre A M, Baranger A, Vallée P, Tanguy X and Renard M (1994) Spontaneous hybridization between a male-sterile oilseed rape and two weeds. *Theoretical and Applied Genetics* 88, 362-368.

Flavell R B, Dart E, Fuchs R L and Fraley R T (1992) Selectable marker genes: safe for plants? *Bio/Technology* 10, 141-144.

Flothmann S and van Aken J (2001) Of maize and men. *EMBO Reports* 2, 644-647.

Frello S, Hansen K R, Jensen J and Jörgensen R B (1995) Inheritance of rapeseed (*Brassica napus*)-specific RAPD markers and a transgene in the cross *B. juncea* x (*B. juncea* x *B. napus*). *Theoretical and Applied Genetics* 91, 236-241.

Fuchs R L, Ream J E, Hammond B G, Naylor M W, Leimgruber R M and Berberich S A (1993) Safety assessment of the neomycin phosphotransferase-II (Npt II) protein. *Bio/Technology* 11, 1543-1547.

Guadagnuolo R, Savova-Bianchi D and Felber F (2001) Gene flow from wheat (*Triticum aestivum* L.) to jointed goatgrass (*Aegilops cylindrica* Host.), as revealed by RAPD and microsatellite markers. *Theoretical and Applied Genetics* 103, 1-8.

Haldrup A, Petersen S G and Okkels F T (1998) The xylose isomerase gene from *Thermoanaerobacterim thermosulfurogenes* allows effective selection of transgenic plant cells using D-xylose as the selection agent. *Plant Molecular Biology* 37, 287-296.

He Z, Fu Y, Si H, Hu G, Zhang S, Yu Y and Sun Z (2004) Phosphomannose-isomerase (pmi) gene as a selectable marker for rice transformation via *Agrobacterium*. *Plant Science* 166, 17-22.

Hendley J O and Ashe K M (2003) Eradication of resident bacteria of normal human skin by antimicrobial ointment. *Antimicrobial Agents in Chemotherapy* 47, 1988-1990.

Herrera-Estrella L, De Block M, Messens E, Hernalsteens J P, Van Montagu M and Schell J (1983) Chimeric genes are dominant selectable markers in plant cells. *The EMBO Journal* 2, 987-995.

Jaiwal P K, Sahoo L, Singh N D and Singh R P (2002) Strategies to deal with the concern about marker genes in transgenic plants: Some environment-friendly approaches. *Current Science* 83, 128-136.

Joersbo M (2001) Advances in the selection of transgenic plants using non-antibiotic marker genes. *Physiologia Plantarum* 111, 269-272.

Joersbo M, Donaldson I, Kreiberg J, Petersen S G, Brundstedt J and Okkels F T (1998) Analysis of mannose selection used for transformation of sugar beet. *Molecular Breeding* 4, 111-117.

Joersbo M, Petersen S G and Okkels F T (1999) Parameters interacting with mannose selection employed for the production of transgenic sugar beet. *Physiologia Plantarum* 105, 109-115.

Kaeppler H F, Menon G K, Skadsen R W, Nuutila A M and Carlson A R (2000) Transgenic oat plants via visual selection of cells expressing green fluorescent protein. *Plant Cell Reports* 19, 661-666.

Lefol E, Fleury A and Darmency H (1996) Gene dispersal from transgenic crops. II. Hybridization between oilseed rape and the wild hoary mustard. *Sexual Plant Reproduction* 9, 189-196.

Lucca P, Ye X and Potrykus 1 (2001) Effective selection and regeneration of transgenic rice plants with mannose as selective agent. *Molecular Breeding* 7, 43-49.

Mikkelsen T R, Andersen B and Jørgensen R B (1996) The risk of crop transgene spread. *Nature* 380, 31.

Mudd S H and Datko A H (1989a) Synthesis of methylated ethanolamine moieties. Regulation by choline in *Lemna*. *Plant Physiology* 90, 296-305.

Mudd S H and Datko A H (1989b) Synthesis of methylated ethanolamine moieties. Regulation by choline in soybean and carrot. *Plant Physiology* 90, 306-310.

Murashige T and Skoog F (1962) A revised medium for rapid growth and bioassay with tobacco tissue cultures. *Physiologia Plantarum* 15, 473-497.

Nap J P, Bijvoet J and Stiekema W (1992) Biosafety of kanamycin-resistant transgenic plants. *Transgenic Research* 1, 239-249.

Nash D, Paleg L G and Wiskich J T (1982) Effect of proline, betaine and some other solutes on the heat stability of mitochondrial enzymes. *Australian Journal of Plant Physiology* 9, 47-57.

Negrotto D, Jolley M, Beer S, Wenck A R and Hansen G (2000) The use of phosphomannose-isomerase as a selectable marker to recover transgenic maize plants (*Zea mays* L.) via *Agrobacterium* transformation. *Plant Cell Reports* 19, 798-803.

Nielsen K M, Bones A M, Smalla K and van Elsas J D (1998) Horizontal gene transfer from transgenic plants to terrestrial bacteria-a rare event? *FEMS Microbiology Reviews* 22, 79-103.

Prasad K V S K, Sharmila P and Pardha Saradhi P (2000) Enhanced tolerance of trans-genic *Brassica juncea* to choline confirms successful expression of the bacterial codA gene. *Plant Science* 159, 233-242.

Puchta H (2003) Marker-free transgenic plants. *Plant Cell, Tissue and Organ Culture* 74, 123-134.

Shah D M, Horsch R B, Klee H J, Kishore G M, Winter J A, Turner N E, Hironaka C M, Sanders P R, Gasser C S, Aykent S, Siegel N R, Rogers S G and Fraley R T (1986) Engineering herbicide tolerance in transgenic plants. *Science* 233, 478-481.

Storey R and Wyn Jones R G (1977) Quaternary ammonium compounds in plants in relation to salt resistance. *Phytochemistry* 16, 447-453.

Summers P S and Weretilnyk E A (1993) Choline synthesis in spinach in relation to salt stress. *Plant Physiology* 103, 1269-1276.

Thimm T, Hoffmann A, Fritz I and Tebbe C C (2001) Contribution of the earthworm *Lumbricus rubellus* (Annelida, Oligochaeta) to the establishment of plasmids in soil bacterial communities. *Microbial. Ecol.* 41, 341-351.

Wang A S, Evans R A, Altendorf P R, Hanten J A, Doyle M C and Rosichan J L (2000) A mannose selection system for production of fertile transgenic maize plants from protoplast. *Plant Cell Reports* 19, 654-660.

Wang W C, Menon G and Hansen G (2003) Development of a novel *Agrobacterium*-mediated transformation method to recover transgenic *Brassica napus* plants. *Plant Cell Reports* 22, 274-281.

Weretilnyk E A, Smith D D, Wilch G A and Summers P S (1995) Enzymes of choline synthesis in spinach. Response of phospho-Base N-methyltransferase activities to light and salinity. *Plant Physiology* 109, 1085-1091.

Wolfenbarger L L and Phifer P R (2000) The ecological risks and benefits of genetically engineered plants. *Science* 290, 2088-2093.

Wright G D (2005) Bacterial resistance to antibiotics: Enzymatic degradation and modification. *Advanced Drug Delivery Reviews* 57, 1451-1470.

Zhang P and Pounti-Kaerlas J (2000) PIG-mediated cassava transformation using positive and negative selection. *Plant Cell Reports* 19, 1041-1048.

Zhang P, Potrykus I and Pounti-Kaerlas J (2000) Efficient production of transgenic cassava using negative and positive selection. *Transgenic Research* 9, 405-415.

The invention claimed is:

1. A selection marker system for distinguishing genetically modified plant cells from wild-type plant cells during caulogenesis and rhizogenesis comprising
    (a) a nucleic acid sequence coding for choline oxidase for genetically modifying at least a part of a plant and;
    (b) at least a part of a wild-type plant of the same plant species, wherein the part of the wild-type plant is a hypocotyl or cotyledonary petiolar explant,
wherein the part of the plant which is genetically modified by the nucleic acid sequence coding for choline oxidase is capable of surviving in a medium containing choline at a concentration which is toxic to the wild-type plant, wherein in the part of the wild-type plant caulogenesis is suppressed at a choline concentration of 20-40 mM and/or rhizogenesis is suppressed at a choline concentration of 30-40 mM.

2. The selection marker system of claim 1, wherein the selection marker system is a positive selection marker system.

3. The selection marker system of claim 1, wherein the plant is selected from the group consisting of *Brassica* sp. and *Nicotiana* sp.

4. The selection marker system of claim 1, wherein genetic modification is done by a method selected from the group consisting of plant cell transformation, transfection, electroporation, DNA injection and cell fusion.

5. The selection marker system of claim 1, wherein choline is provided as suitable salt, in particular in the form of choline chloride, choline acetate, choline sulphate and choline nitrate.

6. A method for screening and/or identifying a choline tolerant plant cell during caulogenesis and rhizogenesis, comprising the steps of
    (a) genetically modifying a plant cell of interest with a nucleic acid coding for choline oxidase, wherein the plant cell is a cotyledonary or hypocotyl plant cell; and
    (b) culturing the genetically modified plant cell in a medium containing choline at a concentration which is toxic to a wild-type of a plant cell of interest;
wherein survival of the genetically modified plant cell during caulogenesis at a choline concentration of 20-40 mM and/or during rhizogenesis at a choline concentration of 30-40 mM is indicative of a choline tolerant plant cell.

7. The method of claim 6, wherein the plant cell is selected from the group consisting of *Brassica* sp. and *Nicotiana* sp.

8. The method of claim 6, wherein genetic modification is done by a method selected from the group consisting of plant cell transformation, transfection, electroporation, DNA injection and cell fusion.

9. The method of claim 6, wherein choline is provided as suitable salt, in particular in the form of choline chloride, choline acetate, choline sulphate and choline nitrate.

* * * * *